(12) United States Patent
Buesseler

(10) Patent No.: US 11,017,929 B2
(45) Date of Patent: *May 25, 2021

(54) MULTI-LAYER SENSOR CORE

(71) Applicant: St. Jude Medical International Holding S.à r.l., Luxembourg (LU)

(72) Inventor: Ryan K. Buesseler, Bristow, VA (US)

(73) Assignee: St. Jude Medical Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/745,081

(22) Filed: Jan. 16, 2020

(65) Prior Publication Data

US 2020/0227192 A1  Jul. 16, 2020

Related U.S. Application Data

(63) Continuation of application No. 15/535,319, filed as application No. PCT/US2015/065383 on Dec. 11, 2015, now Pat. No. 10,573,448.

(60) Provisional application No. 62/090,768, filed on Dec. 11, 2014, provisional application No. 62/128,387, filed on Mar. 4, 2015.

(51) Int. Cl.
| | |
|---|---|
| *G01B 7/00* | (2006.01) |
| *G01D 5/20* | (2006.01) |
| *A61M 25/09* | (2006.01) |
| *H01F 10/13* | (2006.01) |
| *H01F 3/00* | (2006.01) |
| *H01F 5/00* | (2006.01) |
| *A61B 5/06* | (2006.01) |
| *H01F 17/00* | (2006.01) |
| *H01F 3/04* | (2006.01) |
| *H01F 17/04* | (2006.01) |

(52) U.S. Cl.
CPC ............ *H01F 10/131* (2013.01); *A61B 5/062* (2013.01); *G01B 7/003* (2013.01); *G01D 5/2013* (2013.01); *H01F 3/00* (2013.01); *H01F 3/04* (2013.01); *H01F 5/003* (2013.01); *H01F 10/132* (2013.01); *H01F 17/0013* (2013.01); *H01F 17/04* (2013.01); *A61B 2562/0223* (2013.01); *H01F 2017/0066* (2013.01)

(58) Field of Classification Search
CPC ....... A61M 25/09; A61M 25/095; A61B 5/00; A61B 5/05; A61B 5/06; A61B 18/14; G01B 7/00; G01D 5/20
See application file for complete search history.

(56) References Cited

U.S. PATENT DOCUMENTS

| | | |
|---|---|---|
| 5,704,613 A | 1/1998 | Holtkamp |
| 2007/0032746 A1 | 2/2007 | Sell |
| 2007/0259427 A1 | 11/2007 | Storey et al. |
| 2008/0186124 A1 | 8/2008 | Schaffer et al. |
| 2009/0303749 A1 | 12/2009 | Boys et al. |
| 2011/0066029 A1 | 3/2011 | Lyu et al. |
| 2012/0172761 A1 | 7/2012 | Meller et al. |
| 2013/0066194 A1 | 3/2013 | Seter et al. |

(Continued)

*Primary Examiner* — Neel D Shah
(74) *Attorney, Agent, or Firm* — Dykema Gossett PLLC

(57) ABSTRACT

A sensor may include a core and a coil. The core may include a rectangular substrate, a layer of magnetically-permeable material disposed on the substrate, and an adhesive rigidly coupling two ends of the substrate so as to form a tube with the rectangular substrate. The coil may be wound on the tube. The core may further include a layer of radiopaque material. The core may further include a flex pad for electrically coupling the coil with an external system.

20 Claims, 2 Drawing Sheets

(56) References Cited

U.S. PATENT DOCUMENTS

| | | |
|---|---|---|
| 2013/0136847 A1 | 5/2013 | Lee et al. |
| 2013/0169272 A1 | 7/2013 | Eichler et al. |
| 2013/0296692 A1 | 11/2013 | Vanney et al. |
| 2014/0209372 A1 | 7/2014 | Sobe |
| 2014/0225700 A1 | 8/2014 | Doyle et al. |
| 2015/0098152 A1 | 4/2015 | Gadbois et al. |
| 2015/0119862 A1 | 4/2015 | Cajamarca et al. |
| 2015/0335854 A1 | 11/2015 | Dvärsäter et al. |
| 2016/0324474 A1 | 11/2016 | Sterrett et al. |
| 2018/0140800 A1 | 5/2018 | Buesseler et al. |

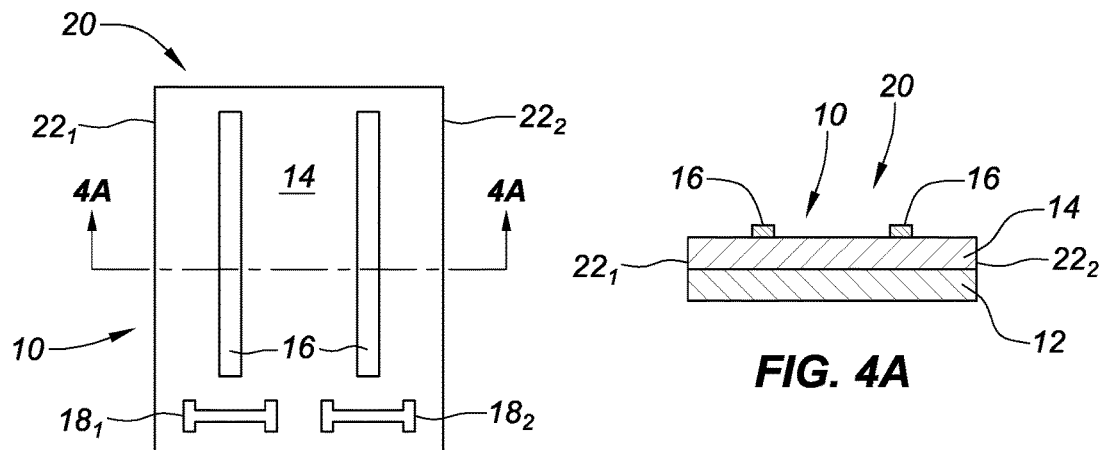
FIG. 4
FIG. 4A
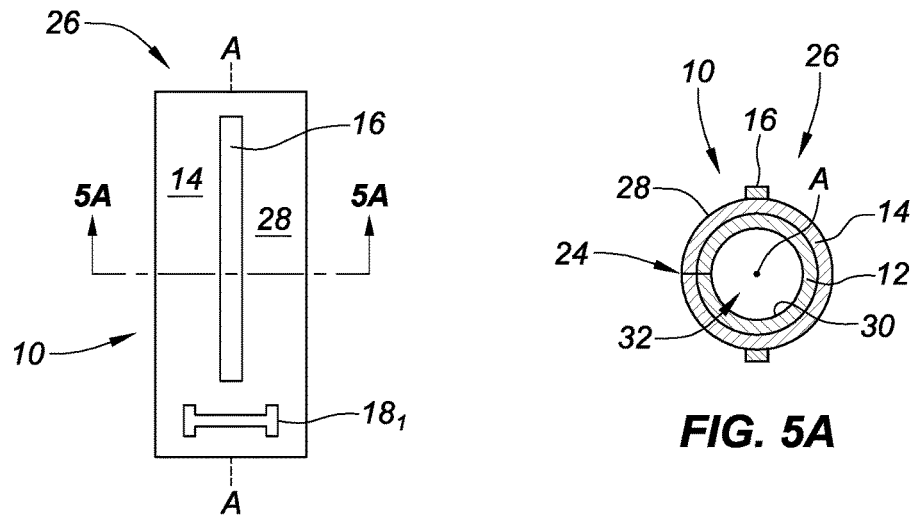
FIG. 5
FIG. 5A
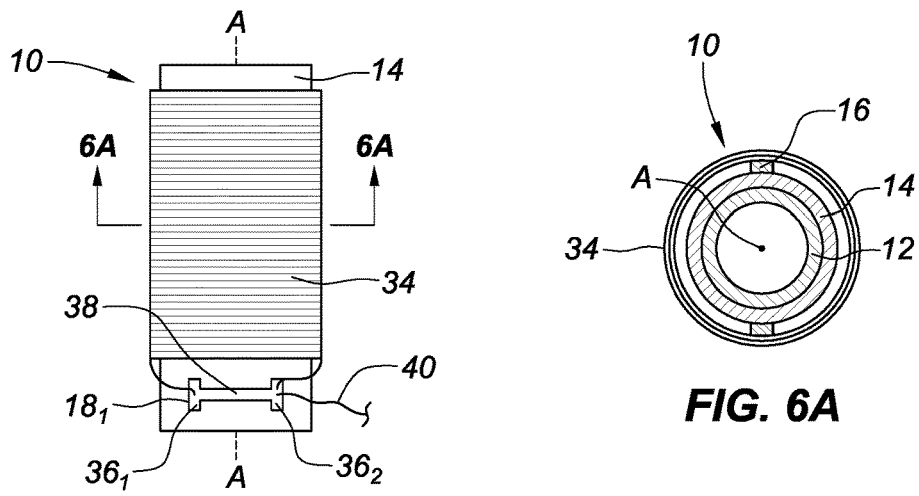
FIG. 6
FIG. 6A

MULTI-LAYER SENSOR CORE

CROSS-REFERENCE TO RELATED APPLICATIONS

This application is a continuation application of U.S. application Ser. No. 15/535,319, filed 12 Jun. 2017 (the '319 application), now U.S. Pat. No. 10,573,448, which is a national stage filing based upon international application no. PCT/US2015/065383, filed 11 Dec. 2015 (the '383 application) which claims the benefit and priority to U.S. provisional application No. 62/090,768, filed 11 Dec. 2014 (the '768 application), and to U.S. provisional application No. 62/128,387, filed 4 Mar. 2015 (the '387 application). The '319 application, the '383 application, the '768 application, and the '387 application are all hereby incorporated by reference in their entirety as though fully set forth herein.

BACKGROUND a. Technical Field

The instant disclosure relates to sensors, including cores for electromagnetic inductance-based position sensors.

b. Background Art

Magnetic field-based position and navigation systems may be used for, among other things, tracking the location of a medical device to navigate the medical device to a target site in a patient's body. Such position and navigation systems operate on the principles of electromagnetic induction. One magnetic field-based position and navigation system is a system incorporating the MediGuide™ technology commercially available from St. Jude Medical, Inc. of St. Paul, Minn. Generally, in magnetic field-based systems, transmitter coils in the system are driven to create a magnetic field. Sensors in the system, which may each include a small inductive coil, are consequently able to detect this magnetic field. These sensors may include coils of wound wire, which in the presence of a magnetic field produce a voltage across the two leads according to the principles of electromagnetic induction.

A general form for an electromagnetic induction positioning sensor includes wire wrapped on a solid or hollow core. In a "solid core" embodiment, the sensor may have a solid cylindrical core. The solid core may be a solid body of material (i.e., with no lumen through the core). The solid core may be made of mu-metal, in an embodiment. The core of a hollow-core sensor may include a tube with a longitudinal lumen (i.e., a hollow cylinder). The core may include mu-metal or polymer, in an embodiment. Known cores are generally made from a single material—either polymer (e.g., polyimide) or mu-metal.

The foregoing discussion is intended only to illustrate the present field and should not be taken as a disavowal of claim scope.

SUMMARY

An exemplary embodiment of a core for a sensor may include a rectangular substrate, a layer of magnetically-permeable material disposed on the substrate, and adhesive for rigidly coupling two ends of said substrate with each other so as to form a hollow cylinder. In an embodiment, the core may further include a layer of radiopaque material.

An exemplary embodiment of a method of manufacturing a core for a sensor may include providing a rectangular substrate, depositing a magnetically-permeable material on the substrate, and rigidly coupling two ends of the substrate with each other so as to form a hollow cylinder.

An exemplary embodiment of a sensor may include a core and a coil. The core may include a rectangular substrate having a top surface, a bottom surface, and four ends, a layer of magnetically-permeable material disposed on at least one of the substrate top surface or the substrate bottom surface, and an adhesive rigidly coupling two of the ends of the substrate so as to form a tube with the rectangular substrate, such that the top surface is an outer surface of the tube and the bottom surface is an inner surface of the tube. The coil may be wound on the tube.

BRIEF DESCRIPTION OF THE DRAWINGS

FIG. 4 is a diagrammatic view of the sensor core portion of FIGS. 1-3, at a later stage of manufacture.

FIG. 4A is a cross-sectional diagrammatic view of the sensor core portion of FIG. 4, taken along line 4A-4A in FIG. 4.

FIG. 5 is a diagrammatic view of the sensor core portion of FIGS. 1-4, at a later stage of manufacture.

FIG. 5A is a diagrammatic cross-sectional view of the sensor core portion of FIG. 5, taken along line 5A-5A in FIG. 5.

FIG. 6 is a diagrammatic view of an exemplary embodiment of a sensor including a coil wound on the sensor core portion of FIG. 5.

FIG. 6A is a cross-sectional diagrammatic view of the sensor of FIG. 6, taken along line 6A-6A of FIG. 6.

DETAILED DESCRIPTION

Figures 1, 1A:
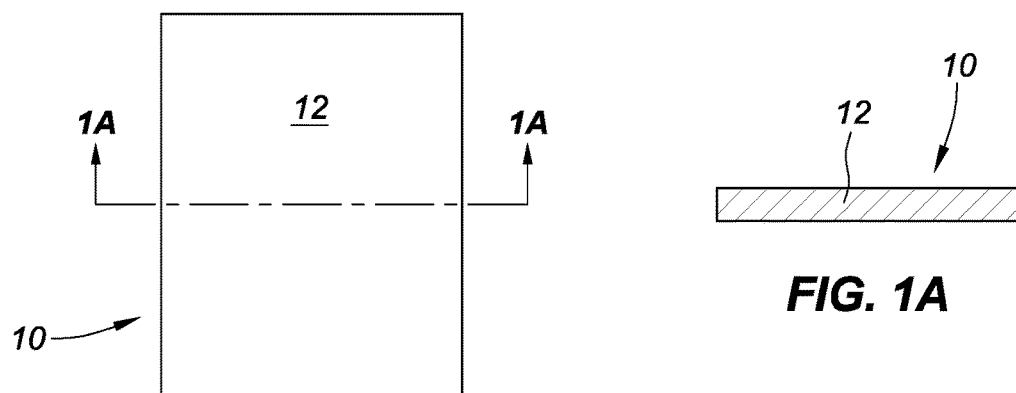
FIG. 1 is a diagrammatic view of an exemplary embodiment of a portion of a core for a sensor at a stage of manufacture.
FIG. 1A is a cross-sectional diagrammatic view of the sensor core portion of FIG. 1, taken along line 1A-1A in FIG. 1.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

The output voltage of an electromagnetic coil sensor (and, thus, the sensitivity of the sensor) is affected by the number of turns of wire in the coil (which may be limited by wire gauge (AWG), core size, and/or other variables), cross-sectional area of the core, and the magnetic permeability of the core. Accordingly, one design feature for a coil sensor that may be altered to increase the sensitivity of the sensor without substantially increasing the size of the sensor is the magnetic permeability of the core. The magnetic permeability of the core may be affected by, among other things, the materials and arrangement of materials that comprise the core.

Referring to the figures in which like reference numerals refer to the same or similar features in the various views, FIGS. 1-6A are diagrammatic and cross-sectional diagrammatic views of various stages of manufacture of a sensor. It should be understood that the term "sensor" may be used herein to refer to both the finished sensor and to portions of the sensor during manufacture.

A sensor as illustrated and/or described herein may find use, for example only, as a position sensor in a magnetic field-based position and navigation system. An exemplary embodiment of such a system, and the use of a sensor in such a system, is set forth in U.S. patent application Ser. No. 13/341,396, filed Dec. 30, 2011, which is hereby incorporated by reference in its entirety. It should be understood, however, that this use is exemplary in nature only. The techniques and arrangements illustrated and/or described in this disclosure may find use with other types of sensors or systems, in embodiments.

Referring to FIGS. 1 and 1A (FIG. 1A is a diagrammatic cross-section view of FIG. 1, taken along line 1A-1A in FIG. 1), manufacture of the sensor 10 may begin with a substrate 12. The substrate 12 may be a monolithic, flat, rectangular sheet of material, in an embodiment. The material may be or may include, for example, nickel and/or titanium (e.g., nitinol) or another highly flexible material. In an embodiment, the substrate 12 may be a thin nitinol film.

Figures 2, 2A:
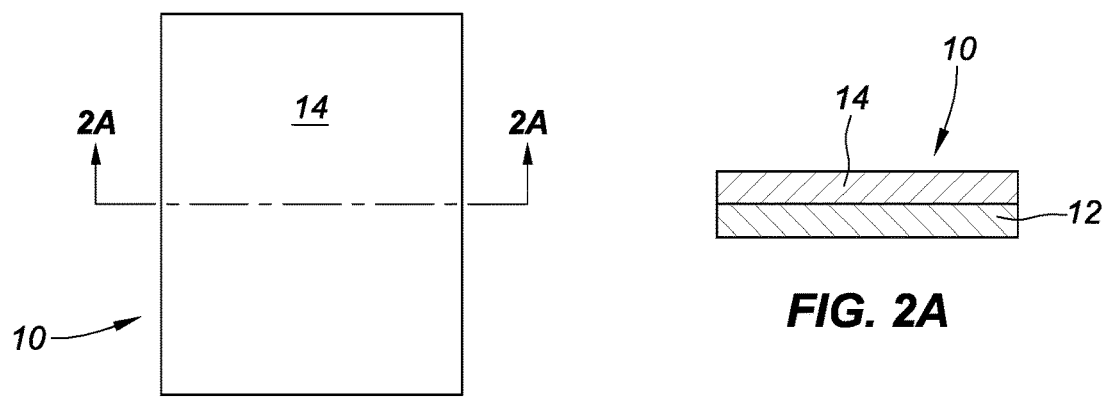
FIG. 2 is a diagrammatic view of the sensor core portion of FIG. 1, at a later stage of manufacture.
FIG. 2A is a cross-sectional diagrammatic view of the sensor core portion of FIG. 2, taken along line 2A-2A in FIG. 2.

As shown in FIGS. 2 and 2A (FIG. 2A is a diagrammatic cross-sectional view of FIG. 2, taken along line 2A-2A in FIG. 2), a layer of radiopaque material 14 may be deposited on the substrate 12. The layer of radiopaque material 14 may be deposited on either (or, in an embodiment, both) the "top" or "bottom" surface of the substrate 12. The radiopaque material 14 may be deposited, for example, via magnetron sputtering and stereo lithography. In embodiments, the radiopaque material 14 may additionally or alternatively be deposited through another appropriate material deposition process, may be printed, or may be applied through a more traditional lamination/epoxy/reflow procedure.

The radiopaque material 14 may be deposited over all or substantially all of one or more sides or surfaces of the substrate 12 (that is, all of the substrate 12 that will be used in the completed sensor 10), in an embodiment. The radiopaque material 14 may be or may include platinum and/or another material that is highly visible under x-ray. For example, the radiopaque material may be or may include silver, gold, tantalum, other precious metals, or ceramic. Additionally, in an embodiment in which the teachings of this disclosure are applied in a non-medical application, the radiopaque material may be or may include lead.

Figures 3, 3A:
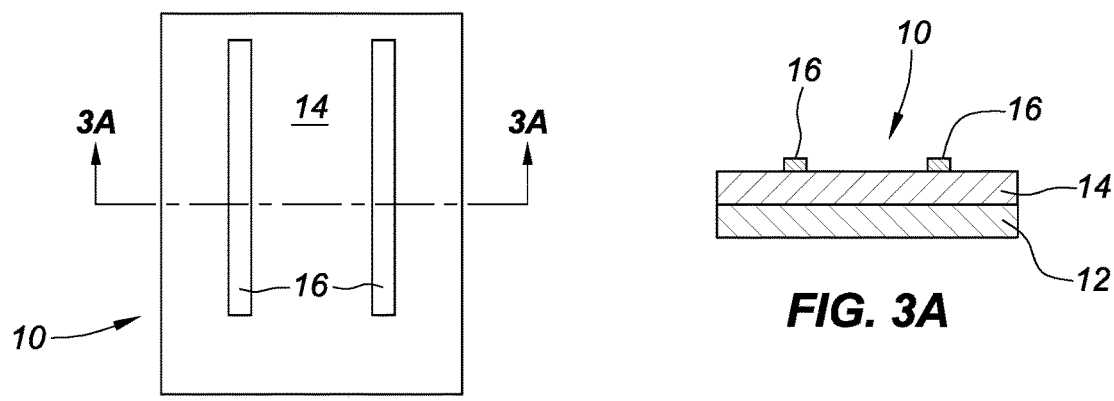
FIG. 3 is a cross-sectional diagrammatic view of the sensor core portion of FIGS. 1 and 2, at a later stage of manufacture.
FIG. 3A is a cross-sectional diagrammatic view of the sensor core portion of FIG. 3, taken along line 3A-3A in FIG. 3.

Referring to FIGS. 3 and 3A (FIG. 3A is a diagrammatic cross-sectional view of FIG. 3, taken along line 3A-3A in FIG. 3), a second layer 16 of magnetically-permeable material may be deposited on the substrate 12 and/or radiopaque material 14.

The second layer 16 may be deposited, for example, via magnetron sputtering and stereo lithography. In embodiments, the second layer 16 may additionally or alternatively be deposited through another appropriate material deposition process, may be printed, or may be applied through a more traditional lamination/epoxy/reflow procedure.

The second layer 16 of material may be or may include a magnetically-permeable material, such as an amorphous magnetic alloy, in an embodiment. The magnetically-permeable material 16 may include various amounts of cobalt, nickel, and iron, in an embodiment. For example, the magnetically-permeable material 16 may be a magnetic alloy commercially available under the trade name Metglas™ from Metglas™, Inc., such as Metglas™ Magnetic Alloy 2714a, or a similar material. The magnetically-permeable material 16 may include approximately 80% cobalt and approximately 20% nickel, iron, and trace elements, in an embodiment. Additionally or alternatively, the magnetically-permeable material may be or may include another material having high relative magnetic permeability (e.g., about 10), such as mu-metal, in an embodiment.

The magnetically-permeable material 16 may be deposited in a predetermined pattern, in an embodiment. For example, the magnetically-permeable material 16 may be deposited in one or more strips or lines that extend parallel with the longitudinal axis of the finished sensor (axis A shown in FIGS. 5, 5A, 6, and 6A). For example, two such strips may be deposited, in an embodiment. Additionally or alternatively, some other pattern or patterns may be deposited. Alternatively, the second layer 16 may be deposited over all or substantially all of one or more sides or surfaces of the radiopaque material 14 and/or substrate 12, in an embodiment.

In an embodiment, a pattern formed by the magnetically-permeable material 16 may be pre-formed and then applied to the assembly. For example, in the illustrated embodiment in which the magnetically-permeable material 16 is provided in two strips or lines, the strips may be fabricated apart from the other layers 12, 14, and then applied to the layers 12, 14.

In an embodiment, the layers 12, 14, 16 of the core may be extruded. Thus, the layers of a multi-layer core may be co-extruded on top of one another. In such an embodiment, the below-described steps of adapting a "flat" sensor core to a tubular sensor may be omitted, as the extrusion steps may result in a tubular core. Furthermore, in an embodiment, the substrate 12 may be a tubular substrate, and the radiopaque material 14 and magnetically-permeable material 16 may be deposited on or applied to the tubular substrate. In such an embodiment, the below-described steps of adapting a "flat" sensor core to a tubular sensor may be omitted.

Although FIGS. 1-3A illustrate an embodiment in which a substrate is at the radial center of the assembly, with radiopaque material on the substrate and magnetically-permeable material on the radiopaque material, this disclosure is not limited to such an arrangement. Rather, in embodiments, the substrate, radiopaque material, and magnetically-permeable material may be arranged in a different order, one of the layers may be omitted, and multiple layers of one or more of the material may be provided, for example. In another exemplary embodiment, the layer of magnetically-permeable material 16 may be provided as an initial layer (a substrate layer, in effect), and radiopaque material 14 and/or other materials may be deposited or printed on or otherwise applied to the magnetically-permeable material 16 to form the structure of a sensor core.

As shown in FIGS. 4 and 4A (FIG. 4A is a diagrammatic cross-sectional view of FIG. 4, taken along line 4A-4A in FIG. 4), flex pads 18 (two such flex pads $18_1$, $18_2$ are illustrated in FIG. 4) may also be placed (e.g., deposited) on the substrate 12 and/or magnetically-permeable material 14. The flex pads 18 may be provided for electrically connecting one or more components of the sensor 10 with separate wiring, in an embodiment.

Two flex pads $18_1$, $18_2$ may be provided, in an embodiment—one $18_1$ for a first end of a wire defining a coil in the finished sensor 10, and a second $18_2$ for the second end of the wire (see FIG. 6). A flex pad 18 may comprise two or more layers, in an embodiment. For example, a first layer of the flex pad 18 may be or may include a thin film of deposited silicon oxide insulator or another dielectric, in an embodiment. A second layer of the flex pad 18 may be or may include gold, or another adequately electrically-conductive material.

The flex pads 18 being incorporated into the core may provide an advantage over known sensors by reducing the number of components needed (i.e., eliminating a separate flex pad or electrical connection means), reducing the number of components that may separately fail. In addition, incorporating the flex pads 18 into the core provides the flex pads with structural support.

Though illustrated as extending orthogonal to the axis A, one or both of the flex pads 18 may extend parallel to the axis A. In such an embodiment, an odd-layer coil may be enabled without the need to extend the wire of the coil "back" for electrical coupling. That is, at least one of the flex pads 18 may provide electrical coupling for the coil at the distal end of the core 20, and may extend longitudinally to a proximal end of the core 20. As a result, the coil may "begin" at the proximal end of the core 20 and "end" at the distal end, with the end wire of the coil electrically coupled to a flex pad 18 that extends longitudinally over the length of the core 20.

The manufacturing steps associated with FIGS. 1-4A may result in a "flat" sensor core 20. The flat core 20 may be used in certain embodiments of a sensor 10. In an embodiment of a magnetic position sensor, the "flat" sensor core 20 may be used to form a tubular sensor core. In an embodiment, the core 20 may have a thickness on the order of thousandths of an inch, for example. In other embodiments, the core 20 may have a thickness that is larger or smaller, depending on the requirements for or desired characteristics of the final device. Two ends of the core $22_1$, $22_2$ may be coupled with each other to form such a tubular core, in an embodiment. For example, in an embodiment, the "flat" core 20 may be rolled and two ends $22_1$, $22_2$ of the flat core may be one or more of laser welded, brazed, otherwise soldered, glued, high-temperature shape-set, rolled, or otherwise bonded or formed to create a hollow cylinder. Accordingly, an adhesive 24 that is used to couple the ends $22_1$, $22_2$ of the flat core 20 may be solder, other filler metal, glue, etc. In the case of a shape-set cylinder, there can be an identifiable longitudinal seam on the outer surface of the cylinder where the two ends $22_1$, $22_2$ of the flat core were joined.

FIGS. 5 and 5A (FIG. 5A is a cross-sectional view of FIG. 5, taken along line 5A-5A in FIG. 5) illustrate the sensor core rolled and bonded to form a hollow cylindrical (i.e., tubular) core 26. As illustrated in FIG. 5A, the radiopaque material 14 may be deposited in a pattern such that the tubular core 26 is visible in an x-ray taken from any direction. Although the tubular core 26 is described here as being formed after the magnetically-permeable material 16 and the radiopaque material 14 have been deposited, in an alternative embodiment the magnetically-permeable material 16 and the radiopaque material 14 can be deposited after formation of the tubular core 26.

Rolling the flat core 20 to form a cylindrical core 26 may result in the "top" of the flat assembly being the outer surface 28 of the tubular core 26, and the "bottom" of the flat assembly being the inner surface 30 of the tubular core 26. The tubular core 26, or one or more layers 12, 14, 16 of the tubular core 26, may define a longitudinal axis A. The substrate 12 may be the radially inner-most layer of the core and may define a longitudinal lumen 32. The layer of magnetically-permeable material 14 may be radially outward of the substrate 12. The layer of radiopaque material 16 may be radially outward of the layer of magnetically-permeable material 14.

Referring to FIGS. 6 and 6A (FIG. 6A is a diagrammatic cross-sectional view of FIG. 6, taken along line 6A-6A in FIG. 6), wire may then be wrapped on the hollow cylinder core to form a coil 34. The coil 34 may include one or more layers of windings, wound at an appropriate pitch and with an appropriate number of layers. For example, the coil 34 may include windings as disclosed in above-referenced U.S. patent application Ser. No. 13/341,396.

As illustrated in FIG. 6, the wire forming the coil 34 may be coupled to the flex pad $18_1$. Each flex pad 18 may include two or more connection pads 36 and an electrically-conductive trace 38 that electrically couples the connection pads 36 to each other, in an embodiment. A first connection pad $36_1$ of a flex pad may be electrically coupled with the wire forming the coil 34, and the second connection pad $36_2$ of the flex pad may be electrically coupled with a wire 40 that may extend to an exterior system (for example, a magnetic field-based position and navigation system), in an embodiment. Wires may be electrically coupled with the flex pad $18_1$ through soldering or welding, in an embodiment. The second flex pad $18_2$ (not shown in FIG. 6) may be similarly electrically coupled with the other end of the wire forming the coil and to the exterior system. In an alternate embodiment, each flex pad 18 may simply comprise a single connection pad 36 to which both the wire forming the coil 34 and the wire 40 that may extend to an exterior system are electrically coupled.

The sensor 10 may be incorporated into an elongate medical device, such as a catheter or introducer, another medical device, or another device. As noted above, the sensor may be connected to a position and navigation system, in an embodiment, to navigate the medical device within a patient's body.

A core including multiple materials and/or multiple layers of material may improve on known coil sensors by improving one or more of, for example, shape retention, magnetic permeability, radiopacity, and ease of electrically coupling the coil with separate wiring relative to single-layer/single-material designs. In particular, the materials comprising the sensor may improve shape retention relative to known sensors, providing a layer of magnetically-permeable material in the core may improve magnetic permeability of a hollow core relative to known hollow-coil sensors, providing a layer of radiopaque material may improve radiopacity relative to known sensors, and providing flex pads on the core may improve ease of electrical coupling.

Although numerous embodiments of this invention have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A core for a sensor, the core comprising:
   a rectangular substrate;
   a layer of magnetically-permeable material disposed on said substrate;
   adhesive for rigidly coupling two ends of said substrate with each other so as to form a hollow cylinder; and
   a flex pad on at least one of (a) said rectangular substrate or (b) said magnetically-permeable material, said flex pad providing an electrical connection for the sensor with an external system; and
   wherein said flex pad comprises:
   a layer of dielectric material disposed on the at least one of (a) said rectangular substrate or (b) said magnetically-permeable material; and
   a layer of electrically-conductive material disposed on said dielectric layer.

2. The core of claim 1, wherein the magnetically-permeable material comprises cobalt and nickel.

3. The core of claim 1, wherein said rectangular substrate includes a top surface and a bottom surface, such that the top surface is an exterior surface of said hollow cylinder and said bottom surface is an interior surface of said hollow cylinder, and further wherein said magnetically-permeable material is disposed on said top surface.

4. The core of claim 3, wherein said magnetically-permeable material covers all of said top surface.

5. The core of claim 1, further comprising a layer of radiopaque material disposed on at least one of (a) said rectangular substrate or (b) said magnetically-permeable material.

6. The core of claim 1, wherein said substrate comprises nitinol.

7. A method of manufacturing a core for a sensor, the method comprising:
   providing a rectangular substrate;
   depositing a magnetically-permeable material on the substrate;
   rigidly coupling two ends of the substrate with each other so as to form a hollow cylinder; and
   creating a flex pad on at least one of (a) the rectangular substrate or (b) the magnetically-permeable material, the flex pad providing an electrical connection for the sensor with an external system; and
   wherein creating the flex pad comprises:
   depositing a layer of dielectric material on the at least one of (a) the rectangular substrate or (b) the magnetically-permeable material; and
   depositing a layer of electrically-conductive material on the layer of dielectric material.

8. The method of claim 7, wherein the magnetically-permeable material comprises cobalt and nickel.

9. The method of claim 7, wherein said rectangular substrate includes a top surface and a bottom surface, such that the top surface is an exterior surface of said hollow cylinder and said bottom surface is an interior surface of said hollow cylinder, and further wherein said magnetically-permeable material is disposed on said top surface.

10. The method of claim 9, wherein the magnetically-permeable material covers all of the top surface.

11. The method of claim 7, further comprising depositing a layer of radiopaque material on at least one of (a) the rectangular substrate or (b) the magnetically-permeable material.

12. The method of claim 7, wherein the substrate comprises nitinol.

13. A sensor comprising:
    a core comprising:
    a rectangular substrate;
    a layer of magnetically-permeable material disposed on said substrate; and
    an adhesive rigidly coupling two ends of said substrate so as to form a tube with said rectangular substrate; and
    a coil wound on said tube;
    wherein said core further comprises an electrically-conductive flex pad on at least one of (a) said rectangular substrate or (b) said magnetically-permeable material, said flex pad providing an electrical connection for the sensor with an external system; and wherein said flex pad comprises:

a layer of dielectric material disposed on the at least one of (a) said rectangular substrate or (b) said magnetically-permeable material; and a layer of electrically-conductive material disposed on said dielectric layer.

14. The sensor of claim 13, wherein said coil is wound on an outer surface of said tube.

15. The sensor of claim 13, wherein said flex pad comprises at least two connection pads and an electrically-conductive trace electrically coupling the two at least two connection pads, wherein said coil is electrically coupled with one of said connection pads.

16. The sensor of claim 13, wherein said substrate comprises nitinol.

17. The sensor of claim 13, wherein said magnetically-permeable layer comprises cobalt and nickel.

18. The sensor of claim 13, wherein said core further comprises a layer of radiopaque material disposed on at least one of (a) said substrate or (b) said layer of magnetically-permeable material.

19. The sensor of claim 13, wherein said rectangular substrate includes a top surface and a bottom surface, such that the top surface is an outer surface of said tube and the bottom surface is an inner surface of said tube, and further wherein said magnetically-permeable material is disposed on said top surface.

20. The sensor of claim 19, wherein said magnetically-permeable material covers all of said top surface.

* * * * *